(12) United States Patent
Alisi et al.

(10) Patent No.: US 8,017,644 B2
(45) Date of Patent: Sep. 13, 2011

(54) 2-ARYLINDOLE DERIVATIVES AS NPGES-1 INHIBITORS

(75) Inventors: Maria Alessandra Alisi, Rome (IT); Nicola Cazzolla, Albano Laziale (IT); Barbara Garofalo, Rome (IT); Guido Furlotti, Rome (IT); Caterina Maugeri, Rome (IT); Rosella Ombrato, San Lorenzo del Vallo (IT); Isabella Coletta, Rome (IT); Lorenzo Polenzani, Grottaferrata (IT); Giorgina Mangano, Rome (IT); Beatrice Garrone, Rome (IT); Angelo Guglielmotti, Rome (IT)

(73) Assignee: Aziende Chimiche Riunite Angelini Francesco A.C.R.A.F. S.p.A., Rome (IT)

(*) Notice: Subject to any disclaimer, the term of this patent is extended or adjusted under 35 U.S.C. 154(b) by 85 days.

(21) Appl. No.: 12/306,426

(22) PCT Filed: Jun. 14, 2007

(86) PCT No.: PCT/EP2007/055901
§ 371 (c)(1),
(2), (4) Date: Dec. 23, 2008

(87) PCT Pub. No.: WO2008/006663
PCT Pub. Date: Jan. 17, 2008

(65) Prior Publication Data
US 2009/0186922 A1     Jul. 23, 2009

(30) Foreign Application Priority Data

Jul. 14, 2006 (IT) .............................. MI2006A1368

(51) Int. Cl.
*A61K 31/405* (2006.01)
*C07D 209/00* (2006.01)
(52) U.S. Cl. ........................................ 514/415; 548/452
(58) Field of Classification Search .................. 514/415; 548/452
See application file for complete search history.

(56) References Cited

U.S. PATENT DOCUMENTS

2004/0180946 A1* 9/2004 Sircar et al. .................... 514/419
2005/0197331 A1* 9/2005 Makovec et al. ........... 514/224.2

FOREIGN PATENT DOCUMENTS

| EP | 1 591 441 | 11/2005 |
|----|-----------|---------|
| WO | 2005/021508 | 3/2005 |
| WO | 2005 021508 | 3/2005 |
| WO | 2005 108369 | 11/2005 |

OTHER PUBLICATIONS

Orr, et al., Journal of the Chemical Society, 1957, 5097-8.*
Orr, et al., J. Chem. Soc., 1957, pp. 5097-8.*

Samir S. Ayobu, et al., "Acetaminophen-induced hypothermia in mice is mediated by a prostaglandin endoperoxide synthase 1 gene-derived protein", PNAS, vol. 101, No. 30, Jul. 27, 2004, pp. 11165-11169.
Andrei I. Ivanov, et al., "Prostaglandin $E_2$-synthesizing enzymes in fever: differential transcriptional regulation", Am. J. Physiol. Regul. Integr. Comp. Physiol., vol. 283, 2002, pp. R1104-R1117.
Maria Domenica Castellone, et al., "Prostaglandin $E_2$ Promotes Colon Cancer Cell Growth Through a $G_s$-Axin-β-Catenin Signaling Axis", Science, vol. 310, Dec. 2, 2005, pp. 1504-1510 and cover page.
Chang Han, et al., "Prostaglandin E2 Receptor EP1 Transactivates EGFR/MET Receptor Tyrosine Kinases and Enhances Invasiveness in Human Hepatocellular Carcinoma Cells", Journal of Cellular Physiology, vol. 207, 2006, pp. 261-270.
Sanjana Mehrotra, et al., "Microsomal prostaglandin $E_2$ synthase-1 in breast cancer: a potential target for therapy", Journal of Pathology, Bol. 208, 2006, pp. 356-363.
Ichiro Kudo, et al., "Prostagandin E Synthase, a Terminal Enzyme for Prostaglandin E2 Biosynthesis", Journal of Biochemistry and Molecular Biology, vol. 38, No. 6, Nov. 2005, pp. 633-638.
Michael Lazarus, et al., "Biochemical Characterization of Mouse Microsomal Prostaglandin E Synthase-1 and its Colocalization with Cyclooxygenase-2 in Peritoneal Macrophages", Archives of Biochemistry and Biophysics, vol. 397, No. 2, Jan. 15, 2002, pp. 336-341.
Makoto Murakami, et al., "Regulation of Prostaglandin $E_2$ Biosynthesis by Inducible Membrane-associated Prostaglandin $E_2$ Synthase That Acts in Concert with Cyclooxygenase-2", The Journal of Biological Chemistry, vol. 275, No. 42, Oct. 2000, pp. 32783-32792. Dirk O. Stichtenoth, et al., "Microsomal Prostaglandin E Synthase Is Regulated by Proinflammatory Cytokines and Glucocorticoids in Primary Rheumatoid Synovial Cells", The Journal of Immunology, vol. 167, 2001, pp. 469-474.
J. R. Vane, et al., "Anti-inflammatory drugs and their mechanism of action", Inflammation Research, vol. 47, Supplement 2, 1998, pp. S78-S87.
D. Wang, et al., "Prostaglandins and Cancer", GUT, vol. 55, 2006, pp. 115-122 and cover page.
Kanato Yamagata, et al., "Coexpression of Microsomal-Type Prostaglandin E Synthase with Cyclooxygenase-2 in Brain Endothelial Cells of Rats suring Endotoxin-Induced Fever". The Journal of Neuroscience, vol. 21, No. 8, Apr. 15, 2001. pp. 2669-2677.
Written Opinion issued in PCT/EP07/055901, Feb. 10, 2007.

* cited by examiner

*Primary Examiner* — Susannah Chung
(74) *Attorney, Agent, or Firm* — Oblon, Spivak, McClelland, Maier & Neustadt, L.L.P.

(57) ABSTRACT

A 2-arylindole compound substituted in position 5, of formula (I): in which X, Y, Z, W, A, R and R' have the meanings given in the description, a pharmaceutical composition comprising it, and also intermediate compounds and a preparation process therefor.

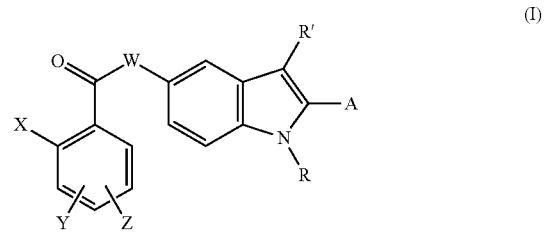

20 Claims, No Drawings

2-ARYLINDOLE DERIVATIVES AS NPGES-1 INHIBITORS

CROSS REFERENCES TO RELATED APPLICATIONS

This application is a 371 of International Patent Application No. PCT/EP2007/055901, filed on Jun. 14, 2007, and claims priority to Italian Patent Application No. MI2006A 001368, filed on Jul. 14, 2006.

The present invention relates to a 2-arylindole compound substituted in position 5, to a pharmaceutical composition comprising it, to intermediate compounds and to a preparation process therefor.

More particularly, the present invention relates to a 2-arylindole compound substituted in position 5, which has inhibitory activity on mPGEs-1.

It is known that prostaglandins (PG) are oxygenated fatty acids synthesized and released into the extracellular space, and then into the plasma, urine and other biological fluids.

They are important bioregulators, but also inflammation mediators that modulate intracellular reactions and intercellular communication.

The prostaglandins $E_2$ ($PGE_2$) have an important physiological role of regulating renal function, vascular homeostasis, bone remodelling, induction of fever, gastrointestinal function and pregnancy. Besides these physiological functions, the $PGE_2$ prostaglandins behave as potent mediators of acute inflammation (inducing hyperalgesia, vasodilatation and discharge of fluids from vessels: Vane J. R. and Botting R. M. 1997 "Anti-inflammatory drugs and their mechanism of action" Inflamm. Res. 47 (2): p. 78) and chronic inflammation. Specifically, the $PGE_2$ prostaglandins are particularly abundant in articular inflammatory pathologies. $PGE_2$ prostaglandins also play a role in pain and are potent pyretic agents (Ayoub S. S. et al., 2004 "A ceta-minophen-induced hypothermia in mice is mediated by a prostaglandin endoperoxide synthase 1 gene-derived protein", PNAS 101: 11165-11169; Ivanov A. et al. 2002 "Prostaglandin $E_2$—synthesizing enzymes in fever: differential transcriptional regulation", Am. J. Physiol. Regul. Integr. Comp. Physiol. 283: R1104-R1117).

The enzyme responsible for the synthesis of $PGE_2$ prostaglandins is prostaglandin E synthase (PGES), which converts the endoperoxide $PGH_2$, formed from arachidonic acid by the action of cyclooxygenases, into $PGE_2$. The activity of PGES has been found both in the cytosolic fraction and membrane-bound in various types of cells.

Three enzymatic forms have been identified (Kudo I. et al. 2005 "Prostaglandin E synthase, a terminal enzyme for prostaglandin $E_2$ biosynthesis", Journal of Biochemistry and Molecular Biology 38, 633-638); among these, microsomial PGES-1 (mPGES-1) is a membrane-bound enzyme that requires glutathione as an essential cofactor for its activity.

The expression of mPGES-1 is induced by pro-inflammatory stimuli such as IL-1β or LPS (Proc. Natl. Acad. Sci. 96: 7220, 1999). It is co-localized together with COX-2 on the endoplasmatic reticum and on the nuclear envelope (Lazarus M. et al. 2002 "Biochemical characterization of mouse microsomal prostaglandin E synthase-1 and its colocalization with cyclooxygenase-2 in peritoneal macrophages" Arch. Biochem. Biophys. 397: 336; Murakami M. et al. 2000 "Regulation of prostaglandin E2 biosynthesis by inducible membrane-associated prostaglandin E2 synthase that acts in concert with cyclooxygenase-2" J. Biol. Chem. 275: 32783; Yamagata K. et al. 2001 "Coexpression of microsomal-type prostaglandin E synthase with cyclooxygenase-2 in brain endothelial cells of rats during endotoxin-induced fever" J. Neurosci. 15; 21(8): 2669-77). Although the two enzymes (COX-2 and mPGES-1) have a functional connection and co-expression, their rate of induction differs in a few cellular systems, indicating different regulatory induction mechanisms (J. Immunol. 167: 469, 2001).

Drugs that inhibit the enzyme COX-2 have been shown to be effective in alleviating inflammation and pain in chronic inflammatory pathologies such as arthritis, but their prolonged use may induce tissue damage caused by an overproduction of cytokines, for instance TNFα and IL-1β (Stichtenoth D. O. 2001 "Microsomal prostaglandin E synthase is regulated by proinflammatory cytokines and glucocorticoids in primary rheumatoid synovial cells" J. Immunol. 167: 469). In addition, the prolonged use of these drugs is associated with cardiovascular side effects. This has led to the withdrawal from the market of a number of selective COX-2 inhibitors and to a revision of the indications for the entire class of these drugs.

Recent research efforts are directed towards overcoming the side effects of COX-2 inhibitors by studying mPGES-1 inhibitors for the purpose of developing drugs that are active in the treatment of inflammation and pain.

In addition, numerous studies have demonstrated that the $PGE_2$ prostaglandins are tumour-promoting factors (Castellone M. D. et al. 2005 "Prostaglandin $E_2$ promotes colon cancer growth through a novel Gs-Axin-B-catenin", Science 310, 1504-1510; Mehrotra S., et al. 2006 "Microsomal prostaglandin $E_2$ in breast cancer: a potential target for therapy", J. Pathol. 208(3): 356-63; Nakano et al. 2006 "Induction of macrophagic prostaglandin E2 synthesis by glioma cells" J. Neurosurgery 104(4), 574-582) that are involved in angiogenesis, cell proliferation and cell migration functions. Selective FANS and COX-2 inhibitors are also found to inhibit various types of tumours, including colorectal, oesophageal, breast, lung and bladder tumours by means of inhibiting $PGE_2$. $PGE_2$ prostaglandins derived from COX-2 induce tumour growth by means of binding to the actual receptors and activating signals for controlling cell proliferation, migration, apoptosis and angiogenesis (Wang D. et al. 2006 "Prostaglandin and cancer" Gut. 55 (1):115-22; Han C. et al. 2006 "Prostaglandin $E_2$ receptor EP1 transactivates EGFR/MET receptor tyrosine kinases and enhances invasiveness in human hepatocellular carcinoma cells", Journal of Cellular Physiology 207: 261-270).

A 2-arylindole compound substituted in position 5 that has selective inhibitory activity on mPGES-1 has now been found.

In a first aspect, the present invention relates to a 2-arylindole compound substituted in position 5, of formula (I):

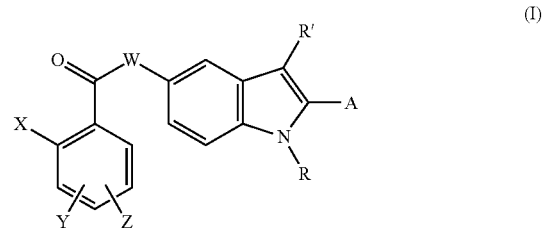

in which:

X is a halogen atom or a ($C_1$-$C_3$)alkyl, trifluoromethyl, nitro, amino, cyano, di($C_1$-$C_3$)alkylamino, hydroxy, ($C_1$-$C_3$)alkoxy, phenyl or ($C_1$-$C_3$)alkylphenyl group;

Y and Z, which may be identical or different, are an H or halogen atom, or a ($C_1$-$C_3$)alkyl, trifluoromethyl, nitro, amino, di($C_1$-$C_3$)alkylamino, hydroxy, ($C_1$-$C_3$)alkoxy, phenyl, COOH, ($C_1$-$C_3$)alkyl-COOH, ($C_2$-$C_3$)alkenyl-COOH, COOR, CONH$_2$, SO$_2$CH$_3$, SO$_2$NHCH$_3$ or NHSO$_2$CH$_3$ group;

W is an O atom or a CH$_2$ or NH group;

R is a hydrogen atom or a ($C_1$-$C_6$)alkyl or ($C_3$-$C_7$)cycloalkyl group optionally substituted with 1 to 3 hydroxy groups;

R' is an H atom or a ($C_1$-$C_6$)alkyl or ($C_3$-$C_7$)cycloalkyl group optionally substituted with 1 to 3 hydroxy groups;

A is a phenyl, naphthyl or pyridine group optionally substituted with 1 to 3 substituents, which may be identical or different, chosen from halogen, ($C_1$-$C_6$)alkyl optionally substituted with 1 to 3 hydroxy groups, trifluoromethyl, nitro, amino, di($C_1$-$C_3$)alkylamino, hydroxy, ($C_1$-$C_3$)alkoxy, benzyloxy, COOH, COOR, SO$_2$CH$_3$, SO$_2$NHCH$_3$, NHSO$_2$CH$_3$, POR$_1$R$_2$, OPOR$_1$R$_2$, ($C_1$-$C_6$) alkyl-COOH, ($C_2$-$C_6$)alkenyl-COOH, phenyl and ($C_1$-$C_3$)alkylphenyl, in which, in turn, R$_1$ and R$_2$, which may be identical or different, are ($C_1$-$C_3$) alkyl; and the physiologically acceptable addition salts, stereoisomers, enantiomers, hydrates, solvates and polymorphic forms thereof.

The chain of the various alkyl groups that may be present in the compound of formula (I) may be linear or branched.

In the case of certain substituents, the compound of formula (I) according to the present invention may contain an asymmetric carbon atom and may thus be in the form of stereoisomers and enantiomers. Typical examples of such substituents are 2-butanol, 2-methylbutyl, 2-butenoic acid, 2-methylpropanoic acid and 1,2-pentane diol.

Preferably, the halogen is bromine, chlorine or fluorine.

Preferred meanings of X are halogen, ($C_1$-$C_3$)alkyl, trifluoromethyl, nitro, cyano and ($C_1$-$C_3$)alkoxy. Particularly preferred meanings of X are Cl, Br, F, trifluoromethyl and nitro.

Preferred meanings of Y and Z are H, halogen, nitro, COOH, ($C_1$-$C_3$)alkyl, trifluoromethyl and ($C_1$-$C_3$)alkoxy. Particularly preferred meanings of Y and Z are Cl, Br, F, trifluoromethyl, nitro, COOH, methyl, ethyl, methoxy and ethoxy.

Preferred meanings of R are methyl, ethyl, propyl, isopropyl and cyclohexyl.

Preferred meanings of R' are H, methyl, ethyl, propyl, isopropyl and cyclohexyl.

Preferred meanings of A are phenyl, naphthyl and pyridine optionally substituted with 1 or 2 substituents, which may be identical or different, selected from halogen, ($C_1$-$C_3$)alkyl, ($C_1$-$C_3$)alkoxy and benzyloxy.

A first particularly preferred meaning of A is phenyl optionally substituted with 1 or 2 substituents, which may be identical or different, selected from Br, Cl, F, methyl, ethyl, methoxy, ethoxy and benzyloxy.

A second particularly preferred meaning of A is naphthyl optionally substituted with 1 or 2 substituents, which may be identical or different, selected from Br, Cl, F, methyl, ethyl, methoxy, ethoxy and benzyloxy.

A third particularly preferred meaning of A is pyridine optionally substituted with 1 or 2 substituents, which may be identical or different, selected from Br, Cl, F, methyl, ethyl, methoxy, ethoxy and benzyloxy.

Depending on the nature of the substituents, the compound of formula (I) may form addition salts with physiologically acceptable organic or mineral acids or bases.

Typical examples of physiologically acceptable mineral acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, succinic acid, tannic acid and tartaric acid.

Typical examples of suitable physiologically acceptable mineral bases are: ammonia, calcium, magnesium, sodium and potassium.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

In a second aspect, the present invention relates to a process for preparing a 2-arylindole compound substituted in position 5, of formula (I):

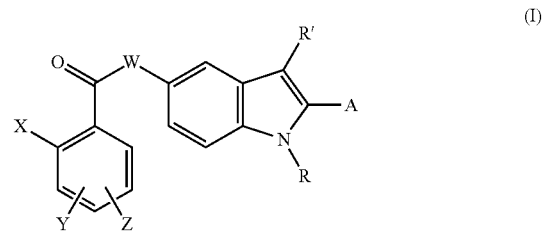

(I)

in which A, X, Y, Z, W, R and R' have the meanings given above, and the physiologically acceptable addition salts, stereoisomers, enantiomers, hydrates, sulfates and polymorphic forms thereof, a) by reacting a compound of formula (II):

(II)

in which
X, Y and Z have the meanings given above, and
Q is a halogen atom or a hydroxy group,
with a compound of formula (III):

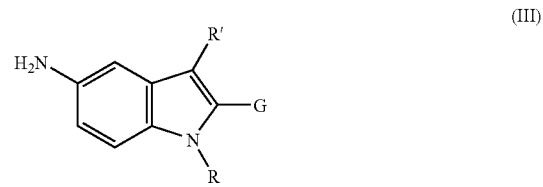

(III)

in which
R and R' have the meanings given above, and
G has the same meanings as A or is a hydrogen atom,
to give a compound of formula (IV):

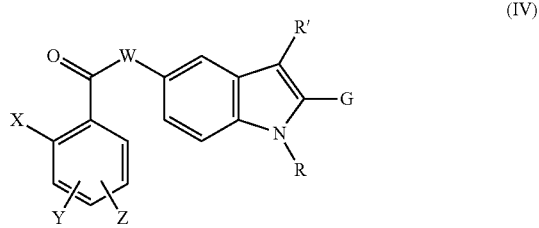

in which
X, Y, Z, W, G, R and R' have the meanings given above, and
b) when G is H, by reacting the compound of formula (IV) with a compound of formula (V):

in which
I is an iodine atom, and
A has the meanings given above, to give the compound of formula (I), and
c) forming, if so desired, a physiologically acceptable addition salt of the compound of formula (IV) from step (a) in which G is other than H or of the compound of formula (I) from step (b).

Clearly, the compound of formula (IV) in which G is other than H is none other than the compound of formula (I). Thus, in the abovementioned step (c), a physiologically acceptable addition salt of the compound of formula (I) of the present invention is always obtained.

According to a first embodiment, the abovementioned step (a) is performed by reacting a compound of formula (II) in which Q is Cl with an amine of formula (III) in the presence of a suitable acid acceptor according to standard techniques.

According to a second embodiment, the abovementioned step (a) is performed by reacting a compound of formula (II) in which Q is OH with an amine of formula (III) in the presence of a suitable coupling agent according to standard techniques.

The reaction in the abovementioned step (b) between a compound of formula (IV) in which G is H and an aryl iodide of formula (V) is also performed according to standard techniques.

The intermediate compounds of formula (III) are novel.

According to a third aspect, the present invention also relates to a compound of formula (III):

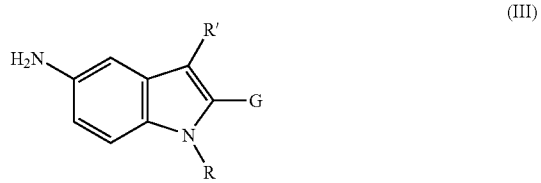

in which
R is a $(C_1-C_6)$alkyl or $(C_3-C_7)$cycloalkyl group optionally substituted with 1 to 3 hydroxy groups;
R' is an H atom or a $(C_1-C_6)$alkyl or $(C_3-C_7)$cycloalkyl group optionally substituted with 1 to 3 hydroxy groups, G is a phenyl, naphthyl or pyridine group optionally substituted with 1 to 3 substituents, which may be identical or different, selected from halogen, $(C_1-C_6)$alkyl optionally substituted with 1 to 3 hydroxy groups, trifluoromethyl, nitro, amino, di$(C_1-C_3)$alkylamino, hydroxy, $(C_1-C_3)$alkoxy, benzyloxy, COOH, COOR, $SO_2CH_3$, $SO_2NHCH_3$, $NHSO_2CH_3$, $POR_1R_2$, $OPOR_1R_2$, $(C_1-C_6)$alkyl-COOH, $(C_2-C_6)$alkenyl-COOH, phenyl and $(C_1-C_3)$alkylphenyl,
in which, in turn,
$R_1$ and $R_2$, which may be identical or different, are $(C_1-C_3)$ alkyl; on condition, however, that G is not an unsubstituted phenyl group when R is methyl and R' is H.

Preferred meanings of R are methyl, ethyl, propyl, isopropyl and cyclohexyl.

Preferred meanings of R' are H, methyl, ethyl, propyl, isopropyl and cyclohexyl.

A first particularly preferred meaning of A is phenyl substituted with 1 or 2 substituents, which may be identical or different, selected from Br, Cl, F, methyl, ethyl, methoxy, ethoxy and benzyloxy.

A second particularly preferred meaning of A is naphthyl optionally substituted with 1 or 2 substituents, which may be identical or different, selected from Br, Cl, F, methyl, ethyl, methoxy, ethoxy and benzyloxy.

A third particularly preferred meaning of A is pyridine optionally substituted with 1 or 2 substituents, which may be identical or different, selected from Br, Cl, F, methyl, ethyl, methoxy, ethoxy and benzyloxy.

The investigations on the biological properties of the compound of formula (I) according to the present invention demonstrated that it has an unexpected selective property of inhibiting mPGES-1 and pronounced anti-nociceptive activity in inflammatory pain.

In a fourth aspect, the present invention thus relates to a pharmaceutical composition containing an effective amount of a compound of formula (I), or of a physiologically acceptable addition salt, stereoisomer, enantiomer, hydrate, solvate or polymorphic form thereof, and at least one pharmaceutically acceptable inert ingredient.

In the present description and in the claims, the term "effective amount" refers to an amount that gives an evaluable improvement in at least one symptom or parameter of a specific disorder.

The pharmaceutical composition according to the present invention will be used in the treatment or prevention of disorders associated with the production of prostaglandin $E_2$ ($PGE_2$), for instance inflammatory processes, pain, tumours, neurodegenerative disorders and atherosclerosis.

Advantageously, the pharmaceutical composition according to the present invention will be used in the treatment of pain in chronic inflammatory pathologies such as arthritis, or of tumours, particularly colorectal, oesophageal, breast, lung and bladder tumours.

Preferably, the pharmaceutical compositions of the present invention are prepared in suitable dosage forms comprising an effective dose of at least one compound of formula (I) or of a physiologically acceptable addition salt, stereoisomer, enantiomer, hydrate, solvate or polymorphic form thereof, and at least one pharmaceutically acceptable inert ingredient.

Examples of suitable dosage forms are tablets, capsules, coated tablets, granules, solutions and syrups for oral administration; creams, ointments and antiseptic plasters for topical administration; suppositories for rectal administration and sterile solutions for administration by injection or aerosol or ophthalmic administration.

The dosage forms may also contain other conventional ingredients, for instance: preserving agents, stabilizers, surfactants, buffers, salts for regulating the osmotic pressure, emulsifiers, sweeteners, colorants, flavourings and the like.

If required for particular therapies, the pharmaceutical composition of the present invention may contain other pharmacologically active ingredients whose simultaneous administration is beneficial.

The amount of compound of formula (I) or of a physiologically acceptable addition salt, stereoisomer, enantiomer, hydrate, solvate or polymorphic form thereof, and at least one pharmaceutically acceptable inert ingredient in the pharmaceutical composition of the present invention may vary within a wide range depending on known factors, for instance the type of disease to be treated, the severity of the disease, the body weight of the patient, the dosage form, the chosen route of administration, the number of daily administrations and the efficacy of the chosen compound of formula (I). However, the optimum amount may be easily and routinely determined by a person skilled in the art.

Typically, the amount of compound of formula (I) or of a physiologically acceptable addition salt, stereoisomer, enantiomer, hydrate, solvate or polymorphic form thereof, and at least one pharmaceutically acceptable inert ingredient in the pharmaceutical composition of the present invention will be such that it provides a level of administration of between 0.0001 and 100 mg/kg/day and even more preferably between 0.01 and 10 mg/kg/day.

Clearly, the pharmaceutical formations of the present invention do not necessarily need to contain the entire amount of the compound of formula (I) since the said effective amount may be added by means of administration of a plurality of doses of the pharmaceutical composition of the present invention.

The dosage forms of the pharmaceutical composition of the present invention may be prepared according to techniques that are well known to pharmaceutical chemists, including mixing, granulation, compression, dissolution, sterilization and the like.

The examples that follow serve to further illustrate the invention without, however, limiting it.

EXAMPLE 1

Preparation of Intermediate Compounds a) 1-methyl-2-phenyl-1H-indol-5-amine

To a solution of 2-phenyl-5-nitroindole (prepared as described in J. Org. Chem. (1966), 31(1), 65-9) (1 g; 4.2 mmol) in DMF (10 ml) was added sodium hydride (50% suspension) (0.20 g; 4.2 mmol); the mixture was left under stirring for 30 minutes.

To the mixture thus obtained was then added dropwise iodomethane (0.60 g; 4.2 mmol) dissolved in DMF (10 ml) and the resulting mixture was left under stirring at room temperature for 18 hours. The mixture was then poured into water (50 ml) and extracted with ethyl acetate (2×50 ml).

The organic phases were combined and dried over $Na_2SO_4$, and the solution was evaporated under reduced pressure. The residue thus obtained was purified by flash chromatography (eluent: 7/3 hexane/ethyl acetate) to give 1 g of 1-methyl-5-nitro-2-phenyl-1H-indole, which was used in the following reaction without any further purification.

$^1$H NMR (300 MHz, DMSO-$d_6$) δ ppm 3.83 (s, 3 H) 6.88 (d, J=0.70 Hz, 1H) 7.47-7.68 (m, 5 H) 7.73 (d, J=9.06 Hz, 1 H) 8.08 (dd, J=9.06, 2.34 Hz, 1 H) 8.59 (d, J=2.05 Hz, 1 H)

To a suspension of 1-methyl-5-nitro-2-phenyl-1H-indole (1 g; 4 mmol) in 95° ethanol (100 ml) was added 10% Pd/C (0.1 g; 0.1 mmol) and the mixture underwent hydrogenation in a Parr hydrogenator (30 psi) for 4 hours.

The reaction mixture was filtered and the solution was evaporated under reduced pressure to give 1-methyl-2-phenyl-1H-indol-5-amine (0.8 g), which was used without any further purification.

$^1$H NMR (300 MHz, DMSO-$d_6$) δ ppm 3.64 (s, 3 H) 4.51 (br, s, 2 H) 6.28 (d, J=0.88 Hz, 1 H) 6.59 (dd, J=8.62, 2.19 Hz, 1 H) 6.70 (d, J=1.46 Hz, 1 H) 7.17 (d, J=8.48 Hz, 1 H) 7.25-7.59 (m, 5 H)

b) 1-ethyl-2-phenyl-1H-indol-5-amine

The process described above in Example 1a) was used, except that iodoethane was used instead of iodomethane.

1-ethyl-5-nitro-2-phenyl-1H-indole: $^1$H NMR (300 MHz, DMSO-$d_6$) δ ppm 1.21 (t, J=7.16 Hz, 3 H) 4.30 (q, J=7.16 Hz, 2 H) 6.83 (d, J=0.58 Hz, 1 H) 7.48-7.63 (m, 5 H) 7.77 (d, J=9.21 Hz, 1 H) 8.07 (dd, J=9.21, 2.34 Hz, 1 H) 8.58 (d, J=2.34 Hz, 1 H)

1-ethyl-2-phenyl-1H-indol-5-amine: $^1$H NMR (300 MHZ, chloroform-d) δ ppm 1.28 (t, J=6.94 Hz, 3 H) 3.59 (br, s, 2 H) 4.13 (q, J=7.16 Hz, 2 H) 6.37 (d, J=0.73 Hz, 1 H) 6.82 (dd, J=8.48, 2.19 Hz, 1 H) 7.09 (d, J=1.90 Hz, 1 H) 7.23 (d, J=8.62 Hz, 1 H) 7.33-7.54 (m, 5 H)

c) 1-isopropyl-2-phenyl-1H-indol-5-amine

The process described above in step a) was used, except that isopropyl bromide was used instead of iodomethane.

1-isopropyl-5-nitro-2-phenyl-1H-indole:
Monoisotopic mass=280.1; LC/MS (M+H)$^+$=281.2 d) 1-ethyl-2-(2-fluorophenyl)-1H-indol-5-amine

To a suspension containing caesium acetate dried under vacuum overnight at 140° C. (3.6 g; 19 mmol) in N,N-dimethylacetamide (DMA, 5 ml), under an inert atmosphere, were added palladium acetate (12 mg; 0.05 mmol), triphenylphosphine (55 mg; 0.21 mmol), 1-ethyl-5-nitro-1H-indole (2 g; 10 mmol) (prepared as described in Bioorg. Med. Chem. 13 (2005), 3531-3541) and 1-iodo-2-fluorobenzene (2.53 g; 11 mmol).

The reaction mixture was left under stirring at 140° C. under an inert atmosphere for 18 hours. The mixture was then cooled to room temperature, dichloromethane (50 ml) was added and the mixture thus obtained was filtered under vacuum through Celite.

The organic solution was transferred into a separating funnel, washed with $H_2O$ (2×50 ml) and dried over $Na_2SO_4$.

The organic solvent was removed by evaporation under reduced pressure and the residue was purified by flash chromatography on silica gel to give 1-ethyl-2-(2-fluorophenyl)-5-nitro-1H-indole (0.7 g), which was used without any further purification.

$^1$H NMR (300 MHz, DMSO-$d_6$) δ ppm 1.15 (t, J=7.16 Hz, 3 H) 4.18 (q, J=7.02 Hz, 2 H) 6.87 (s, 1 H) 7.35-7.50 (m, 2 H) 7.51-7.70 (m, 2 H) 7.79 (d, J=9.06 Hz, 1 H) 8.10 (dd, J=9.06, 2.34 Hz, 1 H) 8.62 (d, J=2.34 Hz, 1 H)

To a suspension containing 1-ethyl-2-(2-fluorophenyl)-5-nitro-1H-indole (0.78 g; 2.75 mmol) in 95° ethanol (100 ml) was added 10% Pd/C (0.1 g; 0.1 mmol) and the mixture underwent hydrogenation in a Parr hydrogenator (30 psi) for 4 hours. The mixture was filtered and the solution was evaporated under reduced pressure to give 1-ethyl-2-(2-fluorophenyl)-1H-indol-5-amine (0.8 g), which was used without any further purification.

e) 1-ethyl-2-(3-fluorophenyl)-1H-indol-5-amine

The process described above in Example 1d) was used, except that 3-fluoro-1-iodobenzene was used instead of 1-iodo-2-fluorobenzene.

1-ethyl-2-(3-fluorophenyl)-5-nitro-1H-indole: $^1$H NMR (300 MHz, DMSO-$d_6$) δ ppm 1.20 (t, J=7.16 Hz, 3 H) 4.32 (q, J=7.31 Hz, 2 H) 6.90 (s, 1 H) 7.31-7.51 (m, 3 H) 7.55-7.67 (m, 1 H) 7.79 (d, J=9.06 Hz, 1 H) 8.09 (dd, J=9.06, 2.34 Hz, 1 H) 8.59 (d, J=2.05 Hz, 1 H)

f) 1-ethyl-2-(4-fluorophenyl)-1H-indol-5-amine

The process described above in Example 1d) was used, except that 4-fluoro-1-iodobenzene was used instead of 1-iodo-2-fluorobenzene.

1-ethyl-2-(4-fluorophenyl)-5-nitro-1H-indole: $^1$H NMR (300 MHz, DMSO-$d_6$) δ ppm 1.19 (t, J=7.16 Hz, 3 H) 4.28 (q, J=7.02 Hz, 2 H) 6.83 (s, 1 H) 7.34-7.45 (m, 2 H) 7.60-7.68 (m, 2 H) 7.77 (d, J=9.35 Hz, 1 H) 8.07 (dd, J=9.35, 2.34 Hz, 1 H) 8.58 (d, J=2.34 Hz, 1 H)

1-ethyl-2-(4-fluorophenyl)-1H-indol-5-amine: $^1$H NMR (300 MHz, chloroform-d) δ ppm 1.24 (t, J=7.16 Hz, 3H) 4.08 (q, J=7.16 Hz, 2 H) 6.33 (s, 1 H) 6.94 (dd, J=8.55, 2.27 Hz, 1 H) 7.09-7.25 (m, 4H) 7.41 (d, J=8.77, 5.41 Hz, 2 H)

g) 1-ethyl-3-methyl-2-phenyl-1H-indol-5-amine

The process described above in Example 1a) was used, except that 2-phenyl-3-methyl-5-nitroindole (prepared as described in Tetrahedron 1965, Vol. 21, 823-829) and iodoethane were used instead of 2-phenyl-5-nitroindole and iodomethane.

1-ethyl-3-methyl-5-nitro-2-phenyl-1H-indole: $^1$H NMR (300 MHz, DMSO-$d_6$) δ ppm 1.10 (t, J=7.10 Hz, 3 H) 2.23 (s, 3 H), 4.16 (q, J=7.27 Hz, 2H) 7.44-7.63 (m, 5 H) 7.71 (d, J=9.25 Hz, 1 H) 8.07 (dd, J=9.25, 2.31 Hz, 1 H) 8.53 (d, J=2.31 Hz, 1 H)

1-ethyl-3-methyl-2-phenyl-1H-indol-5-amine: $^1$H NMR (300 MHz, chloroform-d) δ ppm 1.17 (t, J=7.16 Hz, 3 H) 2.16 (s, 3 H) 3.35 (br, s, 2 H) 4.00 (q, J=7.16 Hz, 2 H) 6.76 (dd, J=8.48, 2.19 Hz, 1 H) 6.96 (d, J=1.75 Hz, 1 H) 7.17 (d, J=8.33 Hz, 1 H) 7.31-7.53 (m, 5 H)

h) 5-amino-2-phenyl-1-cyclohexylindole

To a suspension of caesium acetate dried under vacuum overnight at 140° C. (1.8 g; 9.5 mmol) in N,N-dimethylacetamide (5 ml), under an inert atmosphere, were added palladium acetate (6 mg; 0.05 mmol), triphenylphosphine (28 mg; 0.1 mmol), 1-cyclohexylindole (prepared as described in Synthesis 1977, 5, 335-336) (1 g; 5 mmol) and 1-iodo-4-methylbenzene (1.26 g; 6 mmol).

The reaction mixture was left under stirring at 140° C. under an inert atmosphere for 18 hours. It was then cooled to room temperature and dichloromethane (50 ml) was added. The reaction mixture was filtered under vacuum through Celite. The filtrate was transferred into a separating funnel and the organic phase was washed with $H_2O$ (2×50 ml) and dried over $Na_2SO_4$.

The organic solvent was removed by evaporation under reduced pressure and the residue was purified by flash chromatography on silica gel (97/3 hexane/ethyl acetate) to give 1-cyclohexyl-2-(4-methylphenyl)-1H-indole (200 mg), which was used without any further purification.

$^1$H NMR (300 MHz, chloroform-$d_6$) δ ppm 1.13-1.98 (m, 8 H) 2.25-2.41 (m, 2 H) 2.43 (s, 3 H) 4.21 (tt, J=12.42, 3.80 Hz, 1 H) 6.42 (br. s., 1 H) 7.05-7.11 (m, 1 H) 7.15 (ddd, J=7.90, 7.20, 1.30 Hz, 1 H) 7.22-7.35 (m, 4 H) 7.57-7.67 (m, 2 H)

To a solution of 1-cyclohexyl-2-(4-methylphenyl)-1H-indole (100 mg, 0.3 mmol) in 2 ml of concentrated $H_2SO_4$ at 5° C. was added dropwise a solution of $NaNO_3$ (34 mg; 0.4 mmol) in $H_2SO_4$ (1 ml).

Once the addition was complete, the mixture was left under stirring at 5° C. for 10 minutes. It was then poured into $H_2O$ and ice (10 ml) and the solid thus formed was filtered off and purified by flash chromatography on silica gel (99/1 hexane/ethyl acetate) to give 1-cyclohexyl-2-(4-methylphenyl)-5-nitro-1H-indole (45 mg), which was used without any further purification.

$^1$H NMR (300 MHz, chloroform-d) δ ppm 1.15-1.42 (m, 4 H) 1.64-2.01 (m, 4 H) 2.16-2.41 (m, 2 H) 2.45 (s, 3 H) 4.24 (tt, J=12.42, 3.80 Hz, 1 H) 6.59 (s, 1 H) 7.28-7.35 (m, 4 H) 7.64 (d, J=9.35 Hz, 1 H) 8.06 (dd, J=9.35, 2.34 Hz, 1 H) 8.54 (d, J=2.34 Hz, 1 H)

To a suspension of 1-cyclohexyl-2-(4-methylphenyl)-5-nitro-1H-indole (45 mg; 0.13 mmol) in absolute ethanol (5 ml) was added stannous chloride dihydrate (152 mg; 0.67 mmol) and the mixture was left under stirring at 70° C. for 18 hours. The reaction mixture was cooled to room temperature and then poured into $H_2O$ and ice (20 ml), $NaHCO_3$ (saturated solution) was added to pH 8 and the mixture was left under stirring for 20 minutes.

The mixture was then poured into a separating funnel and extracted with ethyl acetate (2×30 ml). The organic phases were combined and dried over $Na_2SO_4$, and the solvent was removed by evaporation under reduced pressure to give 5-amino-2-(4-methylphenyl)-1-cyclohexylindole (30 mg), which was used without any further purification.

$^1$H NMR (300 MHz, chloroform-$d_6$) δ ppm 1.12-1.42 (m, 4 H) 1.62-1.94 (m, 4 H), 2.17-2.38 (m, 2 H) 2.41 (s, 3 H) 4.05-4.20 (m, 1 H) 4.23 (br. s., 2 H) 6.25 (s, 1 H) 6.69 (dd, J=8.62, 2.19 Hz, 1 H) 6.98 (d, J=2.34 Hz, 1 H) 7.19-7.33 (m, 4 H) 7.45 (d, J=8.77 Hz, 1 H)

i) 2-chloro-N-(1-ethyl-1H-indol-5-yl)benzamide

To a solution of 1-ethyl-1H-indol-5-amine (prepared as described in Bioorg. Med. Chem. 13 (2005), 3531-3541) (27 g; 170 mmol) in dichloromethane (300 ml) was added N,N-diisopropylethylenediamine (26.1 g; 202 mmol), followed by dropwise addition of 2-chlorobenzoyl chloride (35.4 g; 202 mmol) dissolved in dichloromethane (50 ml).

Once the additions were complete, the mixture was left under stirring at room temperature for 2 hours. Water (400 ml) was then added and the organic phase was separated out and dried over $Na_2SO_4$.

The organic solution was evaporated under reduced pressure. The crude product obtained was purified by crystallization with ethyl acetate to give the desired product (37 g).

$^1$H NMR (300 MHz, DMSO-$d_6$) δ ppm 1.35 (t, J=7.27 Hz, 3 H) 4.19 (q, J=7.05 Hz, 2 H) 6.41 (dd, J=2.97, 0.66 Hz, 1 H) 7.34-7.60 (m, 7 H) 8.00 (d, J=1.32 Hz, 1 H) 10.26 (s, 1 H)

EXAMPLE 2

Preparation of Compounds of the Invention a) Example of a First Variant of the Preparation Process:

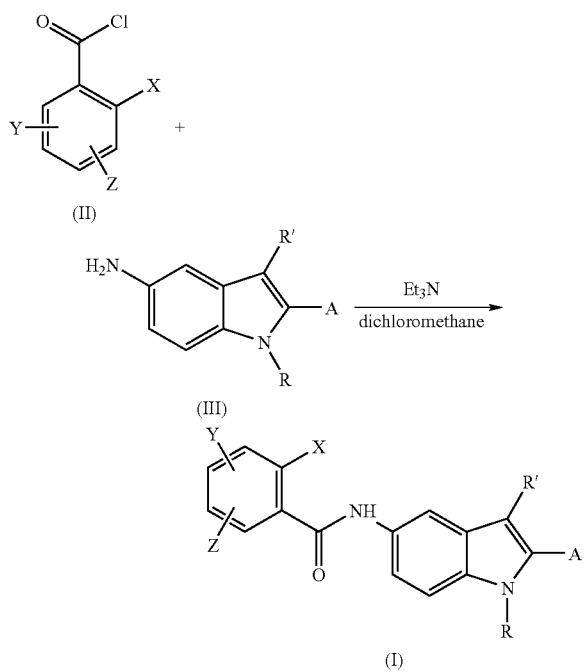

To a solution of a 5-aminoindole (III) (2 mmol) in dichloromethane (10 ml) was added triethylamine (2.2 mmol), followed by dropwise addition of an acyl chloride (II) (2.2 mmol) dissolved in dichloromethane (10 ml). Once the additions were complete, the mixture was left under stirring at room temperature for 20 hours. Water (50 ml) was then added and the organic phase was separated out and dried over $Na_2SO_4$. The solution was evaporated under reduced pressure. The crude product obtained was purified to give compound (I) in which X, Y, Z, R, R' and A have the meanings given above.

b) Example of a Second Variant of the Preparation Process:

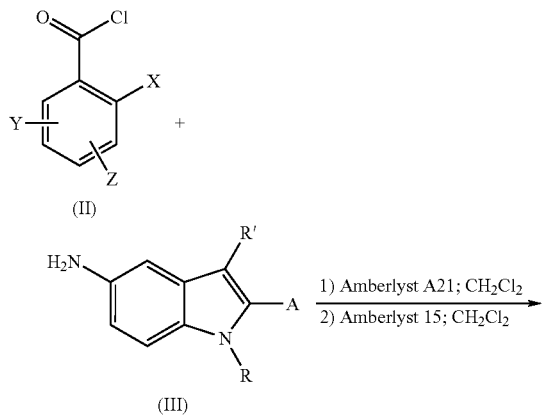

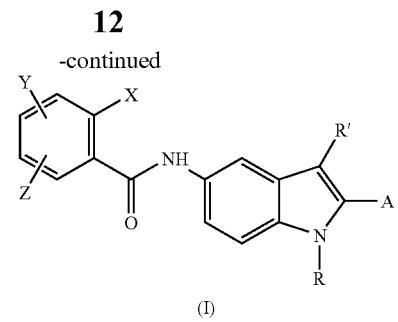

To a suspension of a 5-aminoindole (III) (0.9 mmol) were added Amberlyst A21 resin (0.9 g) in dichloromethane (3 ml) and an acyl chloride (II) (0.28 mmol) in dichloromethane (3 ml). The mixture was left under stirring for 20 hours. The Amberlyst A21 resin was then removed by filtration and washed with dichloromethane (5 ml). The organic phases were combined, diluted with dimethylformamide (1 ml) and stirred with Amberlyst 15 resin (0.9 g) for 5 hours. This treatment was repeated twice. The Amberlyst 15 resin was removed by filtration and the solution was evaporated under centrifuge to give compound (I) in which X, Y, Z, R, R' and A have the meanings indicated above.

c) Example of a Third Variant of the Preparation Process:

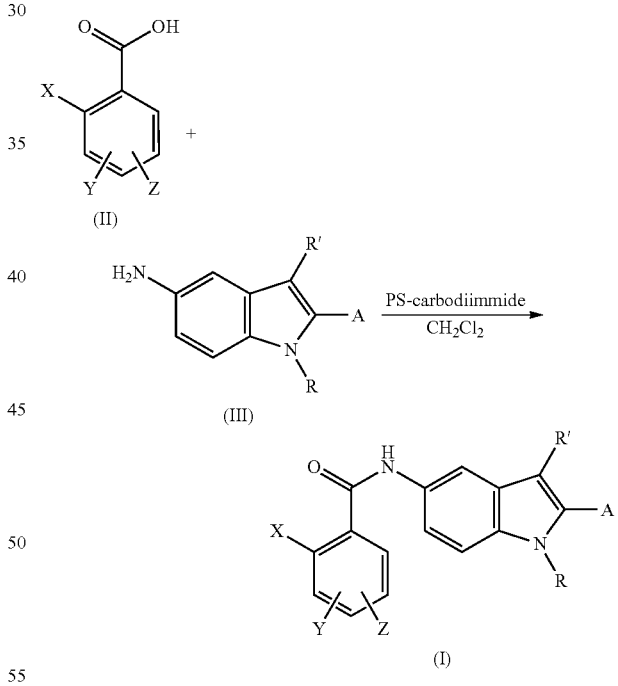

Under an inert atmosphere, a benzoic acid (II) (0.67 mmol) and a 5-aminoindole (III) (0.45 mmol) were dissolved in dichloromethane (8 ml) and dimethylformamide (0.8 ml). After leaving the mixture stirring at room temperature for 10 minutes, PS-carbodiimide resin (0.73 g) was added.

After leaving the reaction mixture stirring for 20 hours, the resin was removed by filtration and washed with dichloromethane (2×5 ml). The solution was evaporated under centrifugation to give compound (I) in which X, Y, Z, R, R' and A have the meanings given above.

d) Example of a Fourth Variant of the Preparation Process:

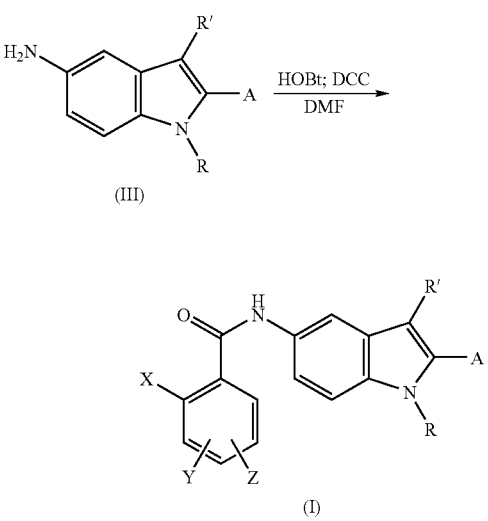

To a solution of a benzoic acid (II) (10 mmol) in dimethylformamide (40 ml) with stirring at 0° C. were added 1-hydroxybenzotriazol (HOBt) (10 mmol) and dicyclohexylcarbodiimide (DCC) (10 mmol). The mixture was left under stirring at 0° C. for 30 minutes and a 5-aminoindole (III) (9 mmol) dissolved in dimethylformamide (20 ml) was added.

The mixture was left under stirring at 0° C. for a further 30 minutes, and then at room temperature for 18 hours. The mixture was filtered, 2N hydrochloric acid was added to pH 2, and the precipitate thus formed was filtered off and purified to give compound (I) in which X, Y, Z, R, R' and A have the meanings given above.

e) Example of a Fifth Variant of the Preparation Process:

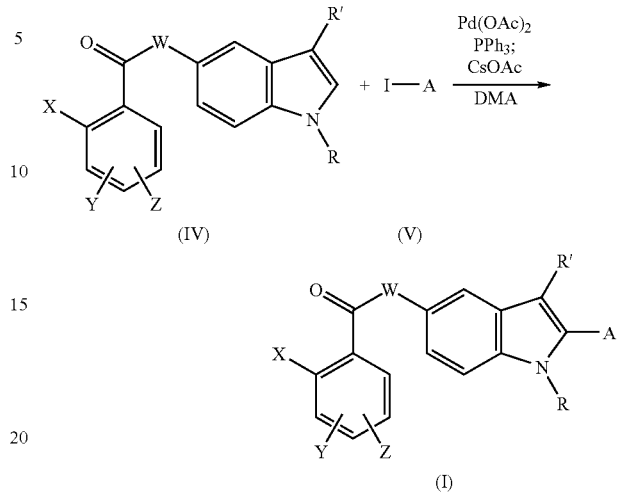

To a suspension of caesium acetate dried under vacuum overnight at 140° C. (6.02 mmol) in N,N-dimethylacetamide (DMA) (3 ml), under an inert atmosphere, were added palladium acetate (0.017 mmol), triphenylphosphine (0.067 mmol), indole (V) (3.35 mmol) and an aryl iodide (V) (3.68 mmol).

The reaction mixture was left under stirring at 140° C. under an inert atmosphere for 18 hours. The reaction mixture was cooled to room temperature, dichloromethane (50 ml) was added and the resulting mixture was filtered under vacuum through Celite. The filtered organic solution was transferred into a separating funnel. The organic phase was washed with $H_2O$ (2×50 ml), dried over $Na_2SO_4$ and evaporated under reduced pressure.

The residue was purified to give compound (I) in which X, Y, Z, R, R' and A have the meanings given above.

The compounds of formula (I) shown in Table 1 below, in which
Purification A=Crystallization
Purification B=Flash chromatography on silica gel
i-PrOH=Isopropanol
$(i-Pr)_2O$=Diisopropyl ether
EtOAc=Ethyl acetate
Hex=Hexane
EtOH=Ethanol
$CHCl_3$=Chloroform
MeOH=Methanol
AcOH=Acetic acid
were thus prepared.

TABLE 1

| Compound | Structural Formula | Example | Purification | Monoisotopic Mass | LC/MS $(M + H)^+$ | $^1$H NMR (300 MHz) |
|---|---|---|---|---|---|---|
| 1 | 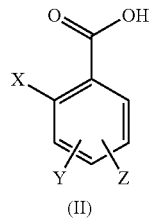 | 2(a) | A (EtOH 95°) | 360.1 | 361.4 | DMSO-$d_6$ δ ppm 3.75 (s, 3 H) 6.58 (s, 1 H) 7.36-7.70 (m, 11 H) 8.06 (s, 1 H) 10.33 (s, 1 H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 2 | | 2(a) | A (i-prOH/ (i-pr)2O =1/1) | 374.1 | 375.4 | DMSO-d6 δ ppm 1.19 (dd, J = 7.00 Hz, 3 H) 4.21 (q, J = 7.10 Hz, 2 H) 6.53 (s, 1 H) 7.39-7.63 (m, 11 H) 8.04 (d, J = 1.65 Hz, 1 H) 10.31 (s, 1 H) |
| 3 | | 2(a) | A (EtOH 95°) | 388.1 | 389.3 | DMSO-d6 δ ppm 1.54 (d, J = 6.95 Hz, 6 H) 4.51-4.68 (m, J = 7.00, 7.00, 7.00, 7.00, 7.00, 7.00 Hz, 1 H) 6.43 (s, 1 H) 7.32-7.72 (m, 11 H) 8.04 (d, J = 1.83 Hz, 1 H) 10.31 (s, 1 H) |
| 4 | | 2(a) | B (Es/AcOEt = 8/2) | | | DMSO-d6 δ ppm 1.13 (t, J = 6.94 Hz, 3 H) 4.08 (q, J = 6.72 Hz, 2 H) 6.54 (s, 1 H) 7.30-7.67 (m, 10 H) 8.07 (d, J = 1.65 Hz, 1 H) 10.34 (s, 1 H) |
| 5 | | 2(a) | B (Es/AcOEt = 8/2) | | | DMSO-d6 δ ppm 1.19 (t, J = 7.10 Hz, 3 H) 4.23 (q, J = 7.27 Hz, 2 H) 6.61 (s, 1 H) 7.23-7.65 (m, 10 H) 8.06 (d, J = 1.98 Hz, 1 H) 10.34 (s, 1 H) |
| 6 | | 2(a) | B (Es/AcOEt = 7/3) | | | DMSO-d6 δ ppm 1.18 (t, J = 7.00 Hz, 3 H) 4.19 (q, J = 7.27 Hz, 2 H) 6.53 (s, 1 H) 7.29-7.67 (m, 10 H) 8.05 (d, J = 1.65 Hz, 1 H) 10.32 (s, 1 H) |
| 7 | | 2(a) | B (Es/AcOEt = 9/1) | | | DMSO-d6 δ ppm 1.08 (t, J = 7.14 Hz, 3 H) 2.16 (s, 3 H) 4.07 (q, J = 7.03 Hz, 2 H) 7.37-7.64 (m, 11 H) 8.02 (d, J = 1.39 Hz, 1 H) 10.32 (s, 1 H) |
| 8 | | 2(a) | B (Es/AcOEt = 9/1) | 442.2 | 443.3 | CHLOROFORM-d δ ppm 1.11-1.44 (m, 4 H) 1.64-1.97 (m, 4 H) 2.23-2.41 (m, 2 H) 2.43 (s, 3 H) 4.20 (tt, J = 12.35, 3.65, 3.51 Hz, 1 H) 6.42 (s, 1 H) 7.21-7.50 (m, 8 H) 7.61 (d, J = 8.77 Hz, 1 H) 7.77-7.84 (m, 1 H) 7.87 (s, 1 H) 7.93 (d, J = 2.05 Hz, 1 H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 9 | 2-(trifluoromethyl)-N-(1-ethyl-2-phenyl-1H-indol-5-yl)benzamide | 2(b) | — | 408.1 | 409.4 | |
| 10 | 2,6-dichloro-N-(1-ethyl-2-phenyl-1H-indol-5-yl)benzamide | 2(b) | — | 408.1 | 409.4 | |
| 11 | 2-methoxy-N-(1-ethyl-2-phenyl-1H-indol-5-yl)benzamide | 2(b) | — | 370.2 | 371.3 | |
| 12 | 2-chloro-5-nitro-N-(1-ethyl-2-phenyl-1H-indol-5-yl)benzamide | 2(c) | — | 419.1 | 420.3 | |
| 13 | 2,5-dichloro-N-(1-ethyl-2-phenyl-1H-indol-5-yl)benzamide | 2(c) | — | 408.1 | 409.4 | |
| 14 | 2-bromo-N-(1-ethyl-2-phenyl-1H-indol-5-yl)benzamide | 2(c) | — | 418.1 | 419.3 | |

TABLE 1-continued

| Compound | Structural Formula | Example | Purification | Monoisotopic Mass | LC/MS (M + H)+ | 1H NMR (300 MHz) |
|---|---|---|---|---|---|---|
| 15 | | 2(c) | — | 354.2 | 355.4 | |
| 16 | | 2(c) | — | 385.1 | 386.3 | |
| 17 | | 2(d) | B CHCl3/MeOH/ AcOH = 95/5/0.1 | 462.1 | 463.3 | DMSO-d6 δ ppm 1.20 (t, J = 7.06 Hz, 3 H) 4.21 (q, J = 6.86 Hz, 2 H) 6.54 (s, 1 H) 7.37-7.61 (m, 7 H) 7.70 (d, J = 7.67 Hz, 1 H) 7.98-8.07 (m, 2 H) 8.17 (d, J = 1.21 Hz, 1 H) 10.42 (s, 1 H) 13.46 (br, s,, 1 H) |
| 18 | | 2(e) | B (Es/AcOEt = 8/2) | 388.1 | 389.3 | DMSO-d6 δ ppm 1.05 (t, J = 7.05 Hz, 3 H) 2.16 (s, 3 H) 3.95 (q, J = 6.97 Hz, 2 H) 6.39 (s, 1 H) 7.26-7.65 (m, 10 H) 8.02 (d, J = 1.57 Hz, 1 H) 10.31 (s, 1 H) |
| 19 | | 2(e) | B (Es/AcOEt = 8/2) | 388.1 | 389.4 | DMSO-d6 δ ppm 1.19 (dd, J = 7.00 Hz, 3 H) 2.40 (s, 3 H) 4.21 (q, J = 6.94 Hz, 2 H) 6.50 (s, 1 H) 7.20-7.67 (m, 10 H) 8.03 (d, J = 1.65 Hz, 1 H) 10.32 (s, 1 H) |
| 20 | | 2(e) | B (Es/AcOEt = 8/2) | 388.1 | 389.2 | DMSO-d6 δ ppm 1.18 (t, J = 6.94 Hz, 3 H) 2.39 (s, 3 H) 4.19 (q, J = 6.94 Hz, 2 H) 6.48 (s, 1 H) 7.28-7.63 (m, 10 H) 8.02 (d, J = 1.65 Hz, 1 H) 10.31 (s, 1 H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 21 | (2-chlorobenzamide N-linked to 5-position of 1-ethyl-2-(4-ethoxyphenyl)indole) | 2(e) | B (Es/AcOEt = 8/2) | 418.1 | 419.4 | DMSO-d6 δ ppm 1.19 (t, J = 7.10 Hz, 3 H) 1.37 (t, J = 6.94 Hz, 3 H) 4.10 (q, J = 6.94 Hz, 2 H) 4.13-4.23 (m, 2 H) 6.44 (s, 1 H) 7.02-7.11 (m, 2 H) 7.24-7.77 (m, 8 H) 8.01 (d, J = 1.65 Hz, 1 H) 10.30 (s, 1 H) |
| 22 | (2-chlorobenzamide N-linked to 5-position of 1-ethyl-2-(4-benzyloxyphenyl)indole) | 2(e) | B (Es/AcOEt = 7/3) | 480.2 | 481.4 | DMSO-d6 δ ppm 1.19 (t, J = 7.02 Hz, 3 H) 4.15-4.22 (m, 2 H) 5.19 (s, 2 H) 6.45 (s, 1 H) 7.12-7.23 (m, 2 H) 7.25-7.64 (m, 13 H) 8.00-8.03 (m, 1 H) 10.30 (s, 1 H) |
| 23 | (2-chlorobenzamide N-linked to 5-position of 1-ethyl-2-(4-tert-butylphenyl)indole) | 2(e) | B (Es/AcOEt = 85/15) | 430.2 | 431.5 | DMSO-d6 δ ppm 1.22 (t, J = 7.10 Hz, 3 H) 1.35 (s, 9 H) 4.20 (q, J = 7.10 Hz, 2 H) 6.49 (s, 1 H) 7.37-7.64 (m, 10 H) 8.03 (d, J = 1.65 Hz, 1 H) 10.31 (s, 1 H) |
| 24 | (2-chlorobenzamide N-linked to 5-position of 1-ethyl-2-(1-naphthyl)indole) | 2(e) | B (Es/AcOEt = 8/2) | 424.1 | 425.3 | DMSO-d6 δ ppm 1.00 (t, J = 7.10 Hz, 3 H) 3.62-4.21 (m, 2 H) 6.57 (d, J = 0.66 Hz, 1 H) 7.41-7.71 (m, 11 H) 8.01-8.12 (m, 3 H) 10.35 (s, 1 H) |
| 25 | (2-chlorobenzamide N-linked to 5-position of 1-ethyl-2-(3-methyl-4-chlorophenyl)indole) | 2(e) | B (Es/AcOEt = 85/15) | 422.1 | 423.2 | DMSO-d6 δ ppm 1.14-1.22 (m, J = 6.94, 6.94 Hz, 3 H) 2.43 (s, 3 H) 4.21 (q, J = 6.94 Hz, 2 H) 6.55 (s, 1 H) 7.36-7.62 (m, 9 H) 8.04 (d, J = 1.65 Hz, 1 H) 10.33 (s, 1 H) |
| 26 | (2-chlorobenzamide N-linked to 5-position of 1-ethyl-2-(4-trifluoromethylphenyl)indole) | 2(e) | B (Es/AcOEt = 8/2) | 442.1 | 443.3 | DMSO-d6 δ ppm 1.20 (t, J = 7.10 Hz, 3 H) 4.25 (q, J = 7.10 Hz, 2 H) 6.68 (s, 1 H) 7.41-7.64 (m, 6 H) 7.76-7.92 (m, 4 H) 8.09 (d, J = 1.65 Hz, 1 H) 10.36 (s, 1 H) |
| 27 | (2-chlorobenzamide N-linked to 5-position of 1-ethyl-2-(3-pyridyl)indole) | 2(e) | B (Es/AcOEt = 7/3) | 375.1 | 376.3 | DMSO-d6 δ ppm 1.20 (t, J = 7.10 Hz, 3 H) 4.22 (q, J = 7.05 Hz, 2 H) 6.66 (s, 1 H) 7.41-7.64 (m, 7 H) 8.00 (dt, J = 8.09, 1.98, 1.82 Hz, 1 H) 8.08 (t, J = 1.88 Hz, 1 H) 8.65 (dd, J = 4.62, 1.65 Hz, 1 H) 8.78 (dd, J = 2.31, 0.99 Hz, 1 H) 10.35 (s, 1 H) |

TABLE 1-continued

| Compound | Structural Formula | Example | Purification | Monoisotopic Mass | LC/MS (M + H)+ | 1H NMR (300 MHz) |
|---|---|---|---|---|---|---|
| 28 | | 2(e) | B (Es/AcOEt = 8/2) | 422.1 | 423.0 | DMSO-d6 δ ppm 1.06 (t, J = 7.10 Hz, 3 H) 2.18 (s, 3 H) 3.94 (br, s,, 2 H) 6.43 (s, 1 H) 7.30-7.63 (m, 9 H) 8.04 (d, J = 1.65 Hz, 1 H) 10.32 (s, 1 H) |
| 29 | | 2(e) | B (Es/AcOEt = 8/2) | 402.1 | 403.3 | DMSO-d6 δ ppm 1.18 (t, J = 7.10 Hz, 3 H) 2.29 (s, 3 H) 2.31 (s, 3 H) 4.19 (q, J = 6.94 Hz, 2 H) 6.46 (s, 1 H) 7.21-7.63 (m, 9 H) 8.02 (d, J = 1.98 Hz, 1 H) 10.30 (s, 1 H) |
| 30 | | 2(e) | B (Es/AcOEt = 8/2) | 404.1 | 405.4 | DMSO-d6 δ ppm 1.19 (t, J = 7.10 Hz, 3 H) 3.83 (s, 3 H) 4.18 (q, J = 6.94 Hz, 2 H) 6.45 (s, 1 H) 7.04-7.13 (m, 2 H) 7.36-7.63 (m, 8 H) 8.01 (d, J = 1.65 Hz, 1 H) 10.30 (s, 1 H) |

EXAMPLE 3

In Vitro Biological Activity

The test used makes it possible to evaluate the inhibitory capacity of the test compounds on the production of $PGE_2$ and the selectivity relative to the production of $PGF_{2\alpha}$. The human pulmonary adenocarcinoma cell line A549 was used, which is particularly sensitive to stimulation with proinflammatory cytokines, for instance $IL-1_\beta$, and, in response to this stimulation, is particularly active in the production and release of two prostanoids: $PGE_2$ and $PGF_{2\alpha}$ (Thoren S. Jakobsson P-J, 2000).

The cells were stimulated with $IL-1_\beta$ (10 ng/ml) and simultaneously treated with the test compound for 22 hours in a suitable culture medium (DMEM—Dulbecco's Modified Eagles Medium) enriched with 5% fetal calf serum and L-glutamine (4 mM final) in an incubator at 37° C. and with a $CO_2$ concentration of 5%.

At the end of the incubation, the amount of $PGE_2$ and $PGF_{2\alpha}$, produced and released into the supernatant were assayed using an EIA kit (produced and sold by Cayman Chemicals, Ann Arbor, Mich., USA).

The comparative compound used was indomethacin at a concentration of 10 nM (Sigma-Aldrich), which is a non-steroidal anti-inflammatory drug that inhibits in equal measure both $PGE_2$ and $PGF_{2\alpha}$.

The results, expressed as a percentage of inhibition of the production of $PGE_2$ and of $PGF_{2\alpha}$ at a concentration of 10 μm, are given in Table 2, in which "ia" (inactive) indicates an inhibitory activity of less than 20%.

TABLE 2

| | % inhibition at 10 μm | |
|---|---|---|
| Compound | $PGE_2$ | $PGF_{2\alpha}$ |
| 1 | 63 | ia |
| 2 | 76 | ia |
| 3 | 91 | 34 |
| 4 | 72 | ia |
| 5 | 91 | 36 |
| 6 | 82 | ia |
| 7 | 90 | 39 |
| 9 | 100 | ia |
| 10 | 76 | ia |
| 12 | 75 | ia |
| 13 | 100 | 36 |
| 16 | 74 | ia |
| 18 | 66 | ia |
| 19 | 87 | 43 |
| 20 | 75 | ia |
| 21 | 66 | ia |
| 22 | 79 | ia |
| 24 | 79 | ia |
| 25 | 89 | ia |
| 28 | 65 | ia |
| 29 | 91 | ia |
| 30 | 75 | ia |
| Indomethacin (10 nM) | 100 | 100 |

For illustrative purposes, Table 3 collates the $pIC_{50}$ values of a number of compounds of the invention, where $pIC_{50}$ represents the negative logarithm of the $IC_{50}$, which, in turn, represents the concentration of compound that inhibits the production of $PGE_2$ or $PGF_{2\alpha}$ by 50% relative to cells that are stimulated but not treated with the same compound.

In Table 3, "nd" means not determinable.

TABLE 3

| Compound | pIC$_{50}$ PGE$_2$ | pIC$_{50}$ PGF$_{2\alpha}$ |
|---|---|---|
| 2 | 5.7 | nd |
| 6 | 5.8 | nd |
| 9 | 5.9 | 4.3 |
| 10 | 5.7 | <4 |
| 13 | 6.1 | nd |
| 18 | 5.6 | nd |
| 19 | 6.0 | 4 |
| 20 | 5.5 | <4 |
| indomethacin | 8.3 | 8.6 |

EXAMPLE 4

In Vivo Biological Activity

The test compound was evaluated in the model of acetic acid-induced stretching in mice (Stock J. L. et al., J Clin Inv 2001, 107: 325-331). This test makes it possible to evaluate the antinociceptive activity of the compounds of the invention in a model of inflammatory pain.

Female CD-1 mice weighing 25-30 g were used for the test. The animals were treated intraperitoneally with the test compound (0.1-10 mg/kg) suspended in methylcellulose (MTC). The control animals were treated with the vehicle alone (MTC) via the same route.

30 minutes after the treatment, the animals received an intraperitoneal injection of acetic acid (0.7 v/v in physiological solution, 16 µl/g of body weight) in order to induce inflammatory pain and to check the effects of the test compound on the nociceptive response.

Immediately after the administration of acetic acid and for the following 20 minutes, the number of stretches, which represents the parameter for evaluation of the nociceptive response, was measured.

As reported in Table 4, the compound of the invention induced, in a dose-dependent manner, a reduction in stretching in the 20 minutes following the administration of acetic acid, compared with the animals treated with MTC alone.

TABLE 4

| Treatment | dose (mg/kg) | No. of stretches | % inhibition |
|---|---|---|---|
| Vehicle | — | 52 | — |
| Compound 2 | 0.1 | 38 | 27 |
|  | 1 | 36 | 31 |
|  | 10 | 25 | 52 |

EXAMPLE 5

Selectivity Between Isoforms of PGES

The test used makes it possible to evaluate the capacity of the compounds of the invention to inhibit the production of PGE$_2$ in a human lymphoma cell line U-937 that preferentially expresses an enzymatic isoform (cPGES), which is responsible for the production of PGE$_2$ under basal conditions, in the absence of pro-inflammatory stimuli. This enzymatic form is different from the one predominantly expressed in the A549 cells (mPGES-1) after a pro-inflammatory stimulus.

The absence of inhibitory activity on PGE$_2$ in this cell model ensures the selectivity of the compound compared with the enzymatic form responsible for the production of PGE$_2$ in the presence of inflammatory stimuli.

The results, expressed as a percentage of inhibition of the production of PGE$_2$, are given in Table 5, in which "ia" (inactive) indicates an inhibitory activity of less than 20%. The reference compound used was indomethacin at a concentration of 10 nM.

The compounds of the invention were found not to significantly inhibit the production of PGE$_2$ owing mainly to the action of cPGES.

TABLE 5

| Compound | % inhibition at 10 µM PGE$_2$ |
|---|---|
| 2 | ia |
| 6 | ia |
| 9 | ia |
| 10 | 22 |
| 13 | 30 |
| 18 | ia |
| 19 | ia |
| 20 | ia |
| Indomethacin (10 nM) | 78 |

The invention claimed is:

1. A compound, of formula (I):

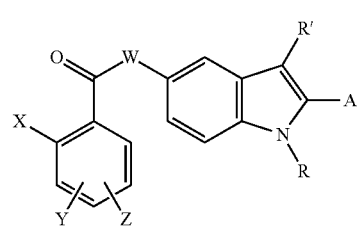

wherein:
X is a halogen atom or a (C$_1$-C$_3$)alkyl, trifluoromethyl, nitro, amino, cyano, di(C$_1$-C$_3$)alkylamino, hydroxy, (C$_1$-C$_3$)alkoxy, phenyl or (C$_1$-C$_3$)alkylphenyl group;
Y and Z, which may be the same or different, are an H or halogen atom, or a (C$_1$-C$_3$)alkyl, trifluoromethyl, nitro, amino, di(C$_1$-C$_3$)alkylamino, hydroxy, (C$_1$-C$_3$)alkoxy, phenyl, COOH, (C$_1$-C$_3$)alkyl-COOH, (C$_2$-C$_3$)alkenyl-COOH, COOR, CONH$_2$, SO$_2$CH$_3$, SO$_2$NHCH$_3$ or NHSO$_2$CH$_3$ group;
W is an O atom or a CH$_2$ or NH group;
R is a hydrogen atom or a (C$_1$-C$_6$)alkyl or (C$_3$-C$_7$)cycloalkyl group optionally substituted with 1 to 3 hydroxy groups;
R' is an H atom or a (C$_1$-C$_6$)alkyl or (C$_3$-C$_7$)cycloalkyl group optionally substituted with 1 to 3 hydroxy groups;
A is a phenyl, naphthyl or pyridine group optionally substituted with 1 to 3 substituents, which may be the same or different, selected from halogen, (C$_1$-C$_6$)alkyl optionally substituted with 1 to 3 hydroxy groups, trifluoromethyl, nitro, amino, di(C$_1$-C$_3$)alkyl amino, hydroxy, (C$_1$-C$_3$)alkoxy, benzyloxy, COOH, COOR, SO$_2$CH$_3$, SO$_2$NHCH$_3$, NHSO$_2$CH$_3$, POR$_1$R$_2$, OPOR$_1$R$_2$, (C$_1$-C$_6$)alkyl-COOH, (C$_2$-C$_6$)alkenyl-COOH, phenyl and (C$_1$-C$_3$)alkylphenyl,
wherein,
R$_1$ and R$_2$, which may be the same or different, are (C$_1$-C$_3$)alkyl;

a physiologically acceptable addition salt thereof, a stereoisomer thereof, or an enantiomer thereof.

2. A compound, physiologically acceptable addition salt, stereoisomer, or enantiomer according to claim 1, wherein X is halogen, $(C_1-C_3)$alkyl, trifluoromethyl, nitro or $(C_1-C_3)$ alkoxy.

3. A compound, physiologically acceptable addition salt, stereoisomer, or enantiomer according to claim 2, wherein X is Cl, Br, F, trifluoromethyl or nitro.

4. A compound, physiologically acceptable addition salt, stereoisomer, or enantiomer according to claim 1, wherein Y and Z are, independently of each other, H, halogen, nitro, COOH, $(C_1-C_3)$alkyl, trifluoromethyl or $(C_1-C_3)$alkoxy.

5. A compound, physiologically acceptable addition salt, stereoisomer, or enantiomer according to claim 4, wherein Y and Z are, independently of each other, Cl, Br, F, trifluoromethyl, nitro, COOH, methyl, ethyl, methoxy or ethoxy.

6. A compound, physiologically acceptable addition salt, stereoisomer, or enantiomer according to claim 1, wherein R is methyl, ethyl, propyl, isopropyl or cyclohexyl.

7. A compound, physiologically acceptable addition salt, stereoisomer, or enantiomer according to claim 1, wherein R' is H, methyl, ethyl, propyl, isopropyl or cyclohexyl.

8. A compound, physiologically acceptable addition salt, stereoisomer, or enantiomer according to claim 1, wherein A is phenyl, naphthyl or pyridine optionally substituted with 1 or 2 substituents, which may be the same or different, selected from halogen, $(C_1-C_3)$alkyl, $(C_1-C_3)$alkoxy and benzyloxy.

9. A compound, physiologically acceptable addition salt, stereoisomer, or enantiomer according to claim 8, wherein A is phenyl optionally substituted with 1 or 2 substituents, which may be the same or different, selected from Br, Cl, F, methyl, ethyl, methoxy, ethoxy and benzyloxy.

10. A compound, physiologically acceptable addition salt, stereoisomer, or enantiomer according to claim 8, wherein A is naphthyl optionally substituted with 1 or 2 substituents, which may be the same or different, selected from Br, Cl, F, methyl, ethyl, methoxy, ethoxy and benzyloxy.

11. A compound, physiologically acceptable addition salt, stereoisomer, or enantiomer according to claim 8, wherein A is pyridine optionally substituted with 1 or 2 substituents, which may be identical or different, selected from Br, Cl, F, methyl, ethyl, methoxy, ethoxy and benzyloxy.

12. A process for preparing a compound of formula (I):

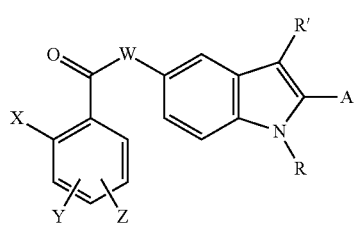

(I)

wherein:
X is a halogen atom or a $(C_1-C_3)$alkyl, trifluoromethyl, nitro, amino, cyano, di$(C_1-C_3)$alkylamino, hydroxy, $(C_1-C_3)$alkoxy, phenyl or $(C_1-C_3)$alkylphenyl group;
Y and Z, which may be identical or different, are an H or halogen atom, or a $(C_1-C_3)$alkyl, trifluoromethyl, nitro, amino, di$(C_1-C_3)$alkylamino, hydroxy, $(C_1-C_3)$alkoxy, phenyl, COOH, $(C_1-C_3)$alkyl-COOH, $(C_2-C_3)$alkenyl-COOH, COOR, CONH$_2$, SO$_2$CH$_3$, SO$_2$NHCH$_3$ or NHSO$_2$CH$_3$ group;

W is an O atom or a CH$_2$ or NH group;
R is a hydrogen atom or a $(C_1-C_6)$alkyl or $(C_3-C_7)$cycloalkyl group optionally substituted with 1 to 3 hydroxy groups;
R' is an H atom or a $(C_1-C_6)$alkyl or $(C_3-C_7)$cycloalkyl group optionally substituted with 1 to 3 hydroxy groups;
A is a phenyl, naphthyl or pyridine group optionally substituted with 1 to 3 substituents, which may be identical or different, selected from halogen, $(C_1-C_6)$alkyl optionally substituted with 1 to 3 hydroxy groups, trifluoromethyl, nitro, amino, di$(C_1-C_3)$alkylamino, hydroxy, $(C_1-C_3)$alkoxy, benzyloxy, COOH, COOR, SO$_2$CH$_3$, SO$_2$NHCH$_3$, NHSO$_2$CH$_3$, POR$_1$R$_2$, OPOR$_1$R$_2$, $(C_1-C_6)$alkyl-COOH, $(C_2-C_6)$alkenyl-COOH, phenyl and $(C_1-C_3)$alkylphenyl,
wherein,
R$_1$ and R$_2$, which may be identical or different, are $(C_1-C_3)$alkyl;
or a physiologically acceptable addition salt thereof;
said process comprising:
a) reacting a compound of formula (II):

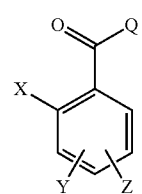

(II)

wherein
X, Y and Z have the meanings given above, and
Q is a halogen atom or a hydroxy group,
with a compound of formula (III):

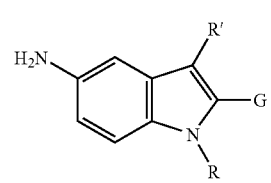

(III)

wherein
R and R' have the meanings given above, and
G has the same meanings as A or is a hydrogen atom,
to obtain a compound of formula (IV):

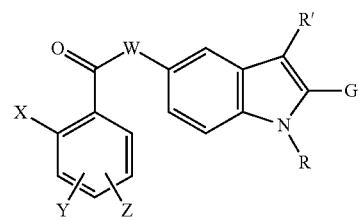

(IV)

wherein
X, Y, Z, W, G, R and R' have the meanings given above;

and b) when G is H, reacting said compound of formula (IV) with a compound of formula (V):

IA—I (V)

wherein

I is an iodine atom, and

A has the meaning given above, to obtain said compound of formula (I); and c) optionally, forming a physiologically acceptable addition salt of said compound of formula (IV) in which G is other than H, or forming a physiologically acceptable addition salt of said compound of formula (I).

13. A process according to claim 12, which comprises reacting a compound of formula (II) in which Q is Cl with said compound of formula (III).

14. A process according to claim 12, which comprises reacting a compound of formula (II) in which Q is OH with said compound of formula (III).

15. A compound of formula (III):

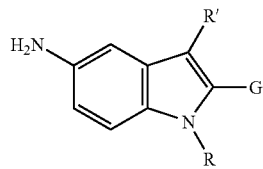

(III)

wherein

R is a $(C_1-C_6)$alkyl or $(C_3-C_7)$cycloalkyl group optionally substituted with 1 to 3 hydroxy groups;

R' is an H atom or a $(C_1-C_6)$alkyl or $(C_3-C_7)$cycloalkyl group optionally substituted with 1 to 3 hydroxy groups, G is a phenyl, naphthyl or pyridine group optionally substituted with 1 to 3 substituents, which may be identical or different, selected from halogen, $(C_1-C_6)$alkyl optionally substituted with 1 to 3 hydroxy groups, trifluoromethyl, nitro, amino, di$(C_1-C_3)$alkylamino, hydroxy, $(C_1-C_3)$alkoxy, benzyloxy, COOH, COOR, $SO_2CH_3$, $SO_2NHCH_3$, $NHSO_2CH_3$, $POR_1R_2$, $OPOR_1R_2$, $(C_1-C_6)$alkyl-COOH, $(C_2-C_6)$alkenyl-COOH, phenyl and $(C_1-C_3)$alkylphenyl, wherein, $R_1$ and $R_2$, which may be identical or different, are $(C_1-C_3)$alkyl;

provided, however, that G is not an unsubstituted phenyl group when R is methyl and R' is H.

16. A compound according to claim 15, wherein R is methyl, ethyl, propyl, isopropyl or cyclohexyl.

17. A compound according to claim 15, wherein R' is H, methyl, ethyl, propyl, isopropyl or cyclohexyl.

18. A pharmaceutical composition, comprising a compound of formula (I):

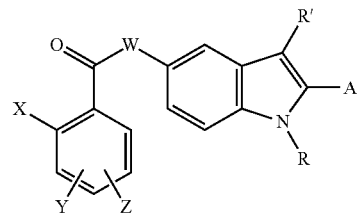

(I)

wherein:

X is a halogen atom or a $(C_1-C_3)$alkyl, trifluoromethyl, nitro, amino, cyano, di$(C_1-C_3)$alkylamino, hydroxy, $(C_1-C_3)$alkoxy, phenyl or $(C_1-C_3)$alkylphenyl group;

Y and Z, which may be identical or different, are an H or halogen atom, or a $(C_1-C_3)$alkyl, trifluoromethyl, nitro, amino, di$(C_1-C_3)$alkylamino, hydroxy, $(C_1-C_3)$alkoxy, phenyl, COOH, $(C_1-C_3)$alkyl-COOH, $(C_2-C_3)$alkenyl-COOH, COOR, $CONH_2$, $SO_2CH_3$, $SO_2NHCH_3$ or $NHSO_2CH_3$ group;

W is an O atom or a $CH_2$ or NH group;

R is a hydrogen atom or a $(C_1-C_6)$alkyl or $(C_3-C_7)$cycloalkyl group optionally substituted with 1 to 3 hydroxy groups;

R' is an H atom or a $(C_1-C_6)$alkyl or $(C_3-C_7)$cycloalkyl group optionally substituted with 1 to 3 hydroxy groups;

A is a phenyl, naphthyl or pyridine group optionally substituted with 1 to 3 substituents, which may be identical or different, selected from halogen, $(C_1-C_6)$alkyl optionally substituted with 1 to 3 hydroxy groups, trifluoromethyl, nitro, amino, di$(C_1-C_3)$ alkylamino, hydroxy, $(C_1-C_3)$alkoxy, benzyloxy, COOH, COOR, $SO_2CH_3$, $SO_2NHCH_3$, $NHSO_2CH_3$, $POR_1R_2$, $OPOR_1R_2$, $(C_1-C_6)$alkyl-COOH, $(C_2-C_6)$alkenyl-COOH, phenyl and $(C_1-C_3)$alkylphenyl, wherein, $R_1$ and $R_2$, which may be identical or different, are $(C_1-C_3)$alkyl;

or a physiologically acceptable addition salt, stereoisomer, or enantiomer thereof, and at least one pharmaceutically acceptable inert ingredient.

19. A pharmaceutical composition according to claim 18, wherein X is halogen, $(C_1-C_3)$alkyl, trifluoromethyl, nitro or $(C_1-C_3)$alkoxy.

20. A pharmaceutical composition according to claim 19, wherein X is Cl, Br, F, trifluoromethyl or nitro.

* * * * *